United States Patent [19]
Lau et al.

[11] Patent Number: 4,827,054
[45] Date of Patent: May 2, 1989

[54] METHOD FOR SYNTHESIZING 2,2-BIS(4-FLUOROPHENYL)-HEXAFLUOROPROPANE AND METHOD FOR USING SAME TO SYNTHESIZE POLY(ARYLETHERS) AND POLY(ARYLTHIOETHERS)

[75] Inventors: Kreisler S. Y. Lau, Alhambra; Thomas K. Dougherty, Irvine, both of Calif.

[73] Assignee: Hughes Aircraft Company, Los Angeles, Calif.

[21] Appl. No.: 221,003

[22] Filed: Jul. 18, 1988

Related U.S. Application Data

[63] Continuation of Ser. No. 81,555, Jul. 31, 1987, abandoned, which is a continuation of Ser. No. 808,402, Dec. 12, 1985, abandoned.

[51] Int. Cl.[4] .................. C07C 17/22; C07C 21/18
[52] U.S. Cl. ............................. 570/141; 528/219
[58] Field of Search ........................................ 570/141

[56]     References Cited
       U.S. PATENT DOCUMENTS 2,606,183  8/1952  Head et al. .................. 570/141
2,705,730  4/1955  Head .......................... 570/141
3,950,444  7/1978  Gay ............................ 570/141
4,096,196  6/1978  Boudakian .................... 570/141
4,503,254  3/1985  Kelleghan ..................... 568/14

FOREIGN PATENT DOCUMENTS 215920  4/1968  U.S.S.R. ........................ 570/141

Primary Examiner—J. E. Evans
Attorney, Agent, or Firm—M. E. Lachman; A. W. Karambelas

[57]              ABSTRACT

Novel processes are provided for synthesizing 2,2-bis(4-fluorophenyl)hexafluoropropane and the use of this synthesized monomer in polymerization reactions to form poly(arylethers) and poly(arylthioethers). Synthesis of 2,2-bis(4-fluorophenyl)hexafluoropropane involves converting the commonly available compound Bisphenol AF to an amino-substituted form, followed by treatment with borofluoric acid and a nitrite, and then an aromatic solvent to obtain the monomer. The monomer can be mixed with either a dihydroxy diphenyl hexafluoropropane or a dimercapto diphenyl hexafluorpropane to cause a nucleophilic substitution reaction, thereby yielding the desired poly(arylether) or poly(arylthioether).

5 Claims, No Drawings

METHOD FOR SYNTHESIZING 2,2-BIS(4-FLUOROPHENYL)-HEXAFLUOROPROPANE AND METHOD FOR USING SAME TO SYNTHESIZE POLY(ARYLETHERS) AND POLY (ARYLTHIOETHERS)

This application is a continuation of application Ser. No. 081,555, filed July 31, 1987 abandoned, which is a continuation of Ser. No. 808,402, filed Dec. 12, 1985 abandoned.

BACKGROUND OF THE INVENTION

Incorporation of hexafluoroisopropylidene(6F) units into a polymer backbone structure assists in the processing of high temperature resistant aromatic heterocyclic polymer systems. These 6F units tend to lower the glass transition temperature (Tg) of polymers prepared therewith and thus improve their melt characteristics. In addition, 6F units wihin a polymer chain prohibit extensive conjugation of aromatic moieties, thereby providing good electric insulation characteristics for the end product resins. Such lack of conjugation also obliterates UV-visible chromophores, thus allowing end product polyimides to appear colorless and to resist photochemical degradation.

Key monomers for the synthesis of thermally stable high temperature resins containing 6F groups have been prepared from commercially available 2,2-bis(4-hydroxyphenyl)hexafluoropropane, commonly known as Bisphenol AF. However, because of the resistance of the hydroxyl functions of Bisphenol AF to replacement by direct chemical modification, the availability of such monomers is severely limited to monomers having substituents which are less reactive than halogen substituents.

Poly(arylethers) and poly(arylthioethers) having as their base monomer units diphenylhexafluoropropanes connected by either oxygen or sulfur linkages are particularly useful polymers, with outstanding mechanical, optical and electrical properties. One method of synthesizing poly(arylethers) and poly(arylthioethers) involves a nucleophilic attack on the para-carbon on the phenyl rings of diphenyl hexafluoropropane. A leaving group, such as one of various halogens, is present on the para-carbon and is displaced during the nucleophilic attack. Of the various halogenated diphenylhexafluoropropanes, difluorinated diphenylhexafluoropropane [2,2-bis(4-fluorophenyl) hexafluoropropane] is the only one that is truly effective because other halogen substituted diphenyl hexafluoropropane compounds do not possess the same reactivity for the desired nucleophilic aromatic substitution reaction in the polymer synthesis.

One apparent method of synthesizing 2,2-bis (4-fluorophenyl)hexafluoropropane is described in U.S. Pat. No. 4,503,254 to Kelleghan, assigned to the same assignee as the present application. The process described in the Kelleghan patent, however, is primarily used to synthesize bromo-substituted diphenyl hexafluoropropanes. The Kelleghan method is not well suited for synthesizing fluoro-substituted diphenyl hexafluoropropane because in such a synthesis, an absolutely anhydrous condition is essential to the reaction. Any variation in the required anhydrous condition will dramatically lower the yield of fluorinated product. It is thus very difficult to obtain an acceptable yield of 2,2-bis(4-fluorophenyl)hexafluoropropane using Bisphenol AF as a starting material.

The synthesis of poly(arylethers) and poly(arylthioethers) can theoretically be performed using halogen-substituted diphenylhexafluoropropanes other than 2,2-bis(4-fluorophenyl)hexafluoropropane, but the yield is extremely poor because such compounds do not possess the desired reactivity for the required nucleophilic aromatic substitution. What is needed, therefore, is a process for synthesizing poly(arylethers) and poly(arylthioethers) using a monomer having a high reactivity for the required nucleophilic aromatic substitution reaction during such synthesis. What is also needed is a method of synthesizing such a monomer in sufficient yield to make its use in the polymerization reaction feasible. The present invention satisfies these needs and provides other related advantages.

SUMMARY OF THE INVENTION

The present invention resides in a novel method for producing 2,2-bis(4-fluorophenyl)hexafluoropropane and a method of using the synthesized hexafluoropropane monomer to produce poly(arylethers) and poly(arylthioethers). The method of the present invention for synthesizing the difluorinated diphenyl hexafluoropropane monomer is extremely advantageous in that a high yield of the monomer is obtained because the reaction is not dependent on the presence of (absolutely) anhydrous conditions. Moreover, the method of the present invention for synthesizing poly(arylethers) and poly(arylthioethers) using 2,2-bis(4-fluorophenyl)hexafluoropropane is a significant advance in the art. The yield of these polymers is substantially increased because of the high reactivity of the synthesized difluorinated monomer in the nucleophilic aromatic substitution reaction that results in polymerization.

More specifically, the method of the present invention for synthesizing 2,2-bis(4-fluorophenyl)hexafluoropropane involves starting with the commonly available compound Bisphenol AF. Using the method disclosed in U.S. Pat. No. 4,370,501 issued to the same inventor and assigned to the same assignee, Bisphenol AF is converted into dianiline form wherein the hydroxy groups on the Bisphenol AF are replaced with amino groups. Basically, this process involves mixing Bisphenol AF with a halogenated quinazoline followed by nucleophilic displacement to yield a bis-quinazoline that is subsequently converted into a bis-quinazolinone and hydrolyzed to form the desired dianiline compound, 2,2-bis(4-aminophenyl)hexafluoropropane.

The dianiline compound is then mixed with fluoroboric acid and sodium nitrite to produce a bis-diazonium salt in which each para carbon on the phenyl rings of the hexafluoropropane compound bears a diazonium($N_2^+$) cation, the gegen-ion being tetrafluoroborate($BF_4^-$). This intermediate bis-diazonium compound is treated with toluene and heated to produce the final monomer product, 2,2-bis (4-fluorophenyl) hexafluoropropane.

The method of the present invention for synthesizing the desired poly (arylethers) comprises mixing the synthesized 2,2-bis(4-fluorophenyl)hexafluoropropane monomer with Bisphenol AF, anhydrous potassium carbonate, distilled sulfolane and anhydrous toluene, thereby generating a bisphenoxide. The bisphenoxide then performs a nucleophilic attack on the para carbon of the phenyl rings on the hexafluoropropane monomer, each of which contains a fluorine leaving group, to produce the desired polymer, the base structural units of which are diphenylhexafluoropropane groups connected by oxygen linkages.

The method of the present invention for synthesizing poly(arylthioethers) is the same as for poly(arylethers), except that 2,2-bis(4-mercaptophenyl)hexafluoropropane is used rather than Bisphenol AF. The resulting polymer has sulfur rather than oxygen linkages due to the mercapto groups on the nucleophilic attacking compound.

In either polymer synthesis, a catalyst can be employed to increase the nucleophilicity of the nucleophilic attacking compound i.e., the bisphenoxide from Bisphenol AF. An example of such a catalyst is dibenzo-18-crown-6.

The final polymers, poly(arylethers) and poly(arylthioethers), are extremely useful, as they have excellent mechanical, optical and electrical properties. Mechanically, these polymers are more processible high temperature resistant polymers, providing various advantages in structural use. Optically, the final polymers are colorless, a distinct advantage when using them as part of a cast film. Electronically, the final polymers are low dielectrics with expected dielectric constant values in the range of $\epsilon = 2-3$, a requirement for materials suitable for high speed electronic circuitry.

The difluoro monomer synthesized by the present invention is also very useful. In addition to being the key element in the polymer synthesis reaction, it could also be used as a high temperature resistant fluid.

The above discussed and many other features and attendant advantages of the present invention will become apparent as the invention becomes better understood by reference to the following detailed description when considered in conjunction with the accompanying drawings.

BRIEF DESCRIPTION OF THE DRAWINGS

FIG. 1 graphically depicts the synthesis of 2,2-bis(4-fluorophenyl)hexafluoropropane in accordance with the present invention.

FIG. 2 graphically depicts the synthesis of poly(arylethers) and poly(arylthioethers) in accordance with the present invention.

DETAILED DESCRIPTION OF THE INVENTION

The present invention is embodied in a novel method for synthesizing 2,2-bis(4-fluorophenyl)hexafluoropropane, which has the following structure:

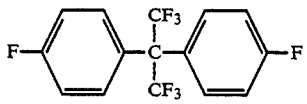

and a novel method for using this synthesized monomer to synthesize poly(arylethers) and poly(arylthioethers), having the basic structure:

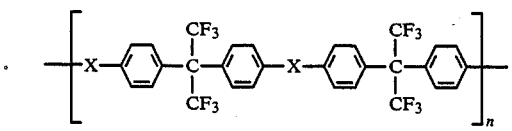

where X=O or S and n is a positive integer whose value depends on the degree of polymerization. The present method of synthesizing the difluorinated monomer has the advantage of not being dependent on the degree to which the reaction is conducted under scrupulously anhydrous conditions, thereby significantly increasing the yield of the desired monomer. The subsequent polymerization reaction using the difluorinated monomer is extremely advantageous as well in that use of this particular monomer is best for the required nucleophilic substitution reaction that occurs during the synthesis, thereby greatly increasing the yield of polymerized products.

More specifically, the preferred embodiment of the present invention's novel synthesis of 2,2-bis(4-fluorophenyl)hexafluoropropane, shown graphically in FIG. 1, begins with the commonly available compound 2,2-bis(4-hydroxylphenyl)hexafluoropropane (1), known as Bisphenol AF. As shown in Example 1, Bisphenol AF is first converted to 2-2,bis(4-aminophenyl)hexafluoropropane (2) by the method described in U.S. Pat. No. 4,370,501, issued to the same inventor and assigned to the same assignee, which is incorporated herein by this reference. Briefly, the method of U.S. Pat. No. 4,370,501 involves mixing Bisphenol AF with 4-chloroquinazoline, followed by nucleophilic displacement to yield a bis-quinazoline that is subsequently thermally rearranged into a bis-quinazolinone and hydrolyzed to form the desired dianiline compound, 2,2-bis(4-aminophenyl)hexafluoropropane. Of course, this compound could be obtained elsewhere by similar variations of the Smiles Rearrangement. Alternatively, the dianiline compound can be synthesized using the corresponding 2,2-bis(4-bromophenyl)hexafluoropropane (described in U.S. Pat. No. 4,503,254) as the starting material in the process described by Trost et al. in the publication "Aziomethyl Phenyl Sulfide: A Synthon for $NH_2^+$," J.Am.Chem. Soc., Vol. 103 (1981) pp. 2483-2485), which involves an apparent amino cation ($NH_2^+$) intermediate. 2,2-bis(4-aminophenyl)hexafluoropropane could then be the starting material in the synthesis.

The dianiline compound is mixed with a fluoride ion donor at about −5° C. to about 10° C., preferably 50 to 70% fluoroboric acid, which is prepared from mixing boric acid and 60 to 75% hydrofluoric acid. An aqueous nitrite solution, preferably sodium nitrite, is then added, preferably dropwise. Another possible fluoride ion donor is antimony hexafluoride, while potassium nitrite might be used rather than sodium nitrite. A yellow bis-diazonium salt (3) is formed, to which is added an aromatic solvent, preferably anhydrous and deaerated toluene at 50° to 80° C., followed by heating to 80° to 110° C. for about one half hour to about one and one half hours to effect nitrogen gas evolution. Other aromatic solvents that might be used include various benzene derivatives, such as the xylenes. After heating at reflux, the organic phase is cooled and extracted with water, saturated sodium bicarbonate and saturated sodium chloride in succession, followed by drying over magnesium sulfate and subsequent concentration. Silica gel column chromatography of the crude resulting oil, with hexane as an eluant, results in a viscous, colorless oil, 2,2-bis(4-fluorophenyl)hexafluoropropane (4), which was identified as indicated in Example 1.

The present invention also includes a method of synthesizing poly(arylethers) and poly(arylthioethers) using the previously synthesized difluoro-substituted monomer. The synthesis involves a nucleophilic substitution reaction which displaces the para-positioned fluorines on the monomer. The reactant that performs the nucleophilic attack on the fluorinated para-carbon of the monomer may either be the anion from 2,2-bis(4-hydroxyphenyl)hexafluoropropane (Bisphenol AF) or the anion from 2,2-bis(4-mercaptophenyl)hexafluoropropane. Using the hydroxy substituted compound will yield a poly(arylether) having oxygen linkages between the diphenyl hexafluoropropane groups, since the oxygen anion from the hydroxy group will nucleophilically displace the fluorine on the monomer. If, on the other hand, the compound used in the reaction is 2,2-bis(4-mercaptophenyl)hexafluoropropane, the final polymer product will be a poly(arylthioether) having sulfur linkages between the diphenylhexafluoropropane groups. This will result from a nucleophilic attack on the fluorinated para-carbon by the sulfur anion from the mercapto group.

As shown in Example 2 and graphically depicted in FIG. 2, the synthesis of the poly(arylether) compound involves mixing Bisphenol AF (5) with 2,2-bis(4-fluorophenyl)hexafluoropropane (4) and an anhydrous carbonate, preferably anhydrous potassium carbonate. Sodium carbonate or lithium carbonate might also be used. A solvent that is stable at high temperatures and a high boiling point aromatic solvent, preferably sulfolane and anhydrous toluene respectively, are then added and the mixture is heated at 125° to 160° C. for one to two hours and then at 180° to 225° C. for three to five hours. An anhydrous xylene might be used rather than anhydrous toluene. Without cooling, the heated mixture is poured into water to form a precipitate. The polymerized precipitate is redissolved in a cyclic ether solvent, preferably tetrahydrofuran, dried with an inorganic drying agent, preferably potassium carbonate, and then reprecipitated in methanol to yield the final polyl(arylether) (6). Other possible cyclic ether solvents include dioxane, tetrahydropyran, and morpholine. Inorganic drying agents that may also be used include magnesium sulfate and sodium sulfate.

The nucleophilic displacement reaction can be aided by using a specific catalyst to increase the nucleophilicity of the hydroxy groups on the Bisphenol AF. In this regard, a crown ether catalyst mixed with a strong base functions well to catalyze the reaction. Crown ether catalysts sold by Aldrich Chemical Co. of Milwaukee, Wis., under the trade names 18-Crown-6 and Dibenzo-18-Crown-6 are suitable for use in this process when a potassium-based phenoxide is used. Synthesis of the poly(arylether) using Dibenzo-18-Crown-6 is shown in Example 3.

In the synthesis of the above-noted polymers, the use of a diphenyl hexafluoropropane substituted with fluorine, as opposed to other halogens, is essential. The fluoro-substituted monomer is the only halogen substituted monomer of this type that has sufficient activity for the required nucleophilic aromatic substitution reaction. These characteristics are demonstrated by Example 5, in which 2,2-bis(4-bromophenyl)hexafluoropropane was used in an attempt to form a polymer. The bromo-substituted monomer was mixed with Bisphenol AF, potassium carbonate, toluene and sulfolane. No solid polymer material was obtained. Similarly, in another run, the bromo-substituted hexafluoropropane was mixed with a potassium salt of Bisphenol AF, sulfolane, dimethylsulfoxide and Dibenzo-18-Crown-6. Even though the crown ether catalyst was used to increase nucleophilicity, no solid polymer material was obtained.

The examples referred to above are shown in detail below.

EXAMPLE 1

Synthesis of 2,2-bis(4-fluorophenyl)hexafluoropropane 2,2-bis(4-aminophenyl)hexafluoropropane was synthesized using the method described in U.S. Pat. No. 4,370,501. Then 16.7 g of 2,2-bis(4-aminophenyl)hexafluoropropane was added to 50 g of 60% fluoroboric acid (prepared from 68 g of boric acid added to 114 g of 70% hydrofluoric acid) at 0° C. Next 6.9 g of sodium nitrite in 25 ml of water was added dropwise to the solution over a period of 0.5 hr. This mixture was slowly stirred for another 0.5 hr and filtered. The resulting yellow bis-diazonium salt was washed successively with 100 ml of cold water and 100 ml of ether. After drying at 0.1 torr overnight, the bis-diazonium salt weighed 21.2 g (39.9 mmoles, 80%). The melting point of the salt was 118° C. (decomposed).

The entire quantity of bis-diazonium salt was added to 200 ml of anhydrous and deaerated toluene at 50° C. The solution was slowly heated to 90° C. to effect gas evolution which persisted for one hour (hr.). The solution was then heated at reflux for an additional two hrs.

After cooling and extracting with water, saturated sodium bicarbonate and saturated sodium chloride in succession, the organic phase was dried over magnesium sulfate and concentrated.

Silica gel column chromatography of the crude oil with hexane as eluant gave a viscous, colorless oil.

Gas liquid chromatography (column OV-101, programmed: initial 160° C. for two minutes, slope 10° C./minute, final 225° C.) showed that the product was 92.3% pure.

Another run of the same quantity was carried out to yield 24.5 g (92%) of the bis-diazonium salt which was thermolyzed in toluene. After silica gel column chromatography purification, the recovered oil was combined with the product of the first run, distilled and recrystallized from hexane. The yield was 18.2 g (53.5 mmoles, 62.2%). The same gas liquid chromatography indicated a purity of >95%. The melting point of the final product was 39.0° C. Test results revealed the following:

IR(Film) 1603 (weak) 1514 (weak), 1259, 1245, 1206, 1176 (strong), 1136, 968, 929, 891 cm$^{-1}$ (medium).

NMR(CDCl$_3$) δ 7.13 (d×d, 4H, J(H$_2$H$_3$)=J(H$_3$F)=8.0 Hz, aromatic H's ortho to F) and 7.37 ppm (broad AB quartet, 4H, aromatic H's ortho to 6F group).

Analysis for C$_{15}$H$_8$F$_8$ (340.213) Calculated: C, 52.96; H, 2.37. Found: C, 53.01; H, 2.47.

EXAMPLE 2

Polymerization of 2,2-bis(4-fluorophenyl)hexafluoropropane to form a poly(arylether)

The reactants comprising 3.36 g of Bisphenol AF, 3.48 g of 2,2-bis(4-fluorophenyl)hexafluoropropane, 4.1 g of anhydrous potassium carbonate (pre-dried at 100° C. for 24 hrs), and a solvent system comprising 50 ml of freshly distilled sulfolane and 20 ml of anhydrous toluene were placed into a dry 100 ml three-neck vessel equipped with a Dean-Stark trap and a nitrogen bubler. The mixture was heated at 140° C. for one hr and then at 200° C. for three hrs. Without cooling, the mixture was poured into 500 ml of water. The water was decanted and the resulting white precipitate was stirred with 500 ml of methanol and filtered. The white powdery solid was redissolved in tetrahydrofuran, dried with potassium carbonate and then reprecipitated in methanol. Test results showed the following:

ηinh=0.07 (30.0° C., THF).

IR (KBr) 1602, 1507, 1251, 1206, 1174, 1137, 969, 927, 830 cm$^{-1}$.

EXAMPLE 3

Polymerization of 2,2-bis(4-fluorophenyl)hexafluoropropane to form a poly(arylether) with addition of dibenzo-18-Crown-6.

The reaction mixture comprising 3.36 g of Bisphenol AF, 3.50 g of 2,2-bis(4-fluorophenyl)hexafluoropropane, 15 ml of sulfolane and 20 mg of dibenzo-18-Crown-6 was placed in a three-neck reaction vessel. The mixture was heated to 120° C. and degassed three times prior to the introduction of 4 g of anhydrous potassium carbonate. The resulting mixture was then heated at 140° C. for one hr and then at 200° C. for three hrs. Without cooling, the mixture was poured into 500 ml of water. The water was decanted and the white precipitate was stirred with 500 ml of methanol and filtered. The white powdery solid was redissolved in tetrahydrofuran, dried with potassium carbonate and then reprecipitated in methanol. Test results on the resulting polymer showed the following:

ηinh=0.07 (30.0° C., THF).

IR (KBr) 1602, 1507, 1251, 1206, 1174, 1137, 969, 927, 830 cm$^{-1}$.

EXAMPLE 4

Polymerization of 2,2-bis(4-fluorophenyl)hexafluoropropane to form a poly(arylether)

The same polymerization process as described in Example 2 was performed using 1.681 g of Bisphenol AF, 1.701 g of 2,2-bis(4-fluorophenyl)hexafluoropropane, 10 ml of sulfolane, 10 ml of toluene and 3 g of anhydrous potassium carbonate. The mixture was heated to 140° C. to distill off toluene, maintained at 140° C. for one hr and then heated at 200° C. for five hrs. Without cooling, the mixture was poured into 500 ml of water. The water was decanted and the white precipitate was stirred with 500 ml of methanol and filtered. The white powdery solid was redissolved in tetrahydrofuran, dried with potassium carbonate and then reprecipitated in methanol. Test results on the final product showed the following:

ηinh=0.11.

IR (KBr) 1602, 1507, 1251, 1206, 1174, 1137, 969, 927, 830 cm$^{-1}$.

EXAMPLE 5

Polymerization using 2,2-bis(4-bromophenyl)hexafluoropropane

Two polymerization runs were performed using 2,2-bis(4-bromophenyl)hexafluoropropane rather than 2,2-bis(4-fluorophenyl)hexafluoropropane. The first run was made using Bisphenol AF as a reaction partner for the bromophenyl compound, in potassium carbonate, toluene and sulfolane. The mixture was heated to 140° C. for one hour and then 200° C. for three hours. No solid polymer material was obtained from this run.

A second run was conducted using a potassium salt of Bisphenol AF as the reaction partner for the bromophenyl compound, in sulfolane, DMSO and dibenzo-18-crown-6. The mixture was heated at 175° C. for two hours, and again no solid polymer material was obtained.

It is apparent from the foregoing description that the two synthesis methods of the present invention provide significant advantages over the prior art. The use of 2,2-bis(4-fluorophenyl)hexafluoropropane in the synthesis of poly(arylethers) and poly(arylthioethers) greatly increases the yield of final product. The method for synthesizing the fluoro-substituted monomer is therefore extremely important with respect to enabling the polymer synthesis to be performed. This method produces the fluoro-substituted monomer in substantially higher yield than prior art methods, some of which work for other halogens but do not work at all for fluorine.

Having thus described exemplary embodiments of the present invention, it should be noted by those skilled in the art that the within disclosures are exemplary only and that various other alternatives, adaptations and modifications may be made without departing from the scope of the present invention. Accordingly, the present invention is not limited to the specific embodiments as illustrated herein, but is only to be limited by the following appended claims.

What is claimed is:

1. A method of synthesizing 2,2-bis(4-fluorophenyl)-hexafluoropropane comprising the steps of:
   (a) treating 2,2-bis(4-aminophenyl)hexafluoropropane with a sufficient amount of fluoride ion donor and a sufficient amount of a nitrite at a temperature within the range of about −5° C. to 10° C. to form a bis-diazonium salt; and
   (b) treating said bis-diazonium salt with a solvent selected from the group consisting of toluene and xylene at a temperature within the range of about 80° C. to 110° C. and for about 0.5 to 1.5 hours to form 2,2-bis(4-fluorophenyl)hexafluoropropane.

2. The method as set forth in claim 1 wherein said fluoride ion donor in step "a" is fluoroboric acid.

3. The method as set forth in claim 1 wherein said nitrite in step "a" is sodium nitrite.

4. The method as set forth in claim 1 wherein said aromatic solvent in step "b" is toluene.

5. The method as set forth in claim 1 including the further step of separating said 2,2-bis(4-fluorophenyl)-hexafluoropropane from said solvent.

* * * * *